United States Patent
Rotter et al.

(10) Patent No.: US 12,376,948 B2
(45) Date of Patent: Aug. 5, 2025

(54) ULTRASONIC CLEANING DEVICE

(71) Applicants: Novosonic Ltd., Bnei Brak (IL); Shlomo Rotter, Kfar Bilu (IL); Tahel Altman, Ramat Hasharon (IL); Yaniv Lambaz, Tel Aviv (IL)

(72) Inventors: Shlomo Rotter, Kfar Bilu (IL); Tahel Altman, Ramat Hasharon (IL); Yaniv Lambaz, Tel Aviv (IL)

(73) Assignee: Dimoveo Medical Ltd., Or Yehuda (IL)

( * ) Notice: Subject to any disclaimer, the term of this patent is extended or adjusted under 35 U.S.C. 154(b) by 1025 days.

(21) Appl. No.: 17/420,206

(22) PCT Filed: Jan. 3, 2020

(86) PCT No.: PCT/IL2020/050008
§ 371 (c)(1),
(2) Date: Jul. 1, 2021

(87) PCT Pub. No.: WO2020/141532
PCT Pub. Date: Jul. 9, 2020

(65) Prior Publication Data
US 2022/0160483 A1    May 26, 2022

Related U.S. Application Data

(60) Provisional application No. 62/787,910, filed on Jan. 3, 2019.

(51) Int. Cl.
*A61C 17/20* (2006.01)
*A61C 17/02* (2006.01)
(Continued)

(52) U.S. Cl.
CPC .......... *A61C 17/20* (2013.01); *A61C 17/0202* (2013.01); *A61C 17/028* (2013.01);
(Continued)

(58) Field of Classification Search
None
See application file for complete search history.

(56) References Cited

U.S. PATENT DOCUMENTS 3,401,690 A    9/1968   Martin
4,991,570 A    2/1991   Bullard
(Continued)

FOREIGN PATENT DOCUMENTS

WO    WO-0053341 A1 *   9/2000   ............. A61B 1/121

OTHER PUBLICATIONS

PCT Search Report and Written Opinion PCT/IL2020/050008, Apr. 6, 2020.

*Primary Examiner* — Cristi J Tate-Sims
(74) *Attorney, Agent, or Firm* — Dekel Patent Ltd.; David Klein

(57) ABSTRACT

Ultrasonic cleaning methods may be enhanced by adding certain particles to a liquid through which ultrasonic waves travel through. Specifically, metal nitrites, metal carbides, and metal oxide particles may be used separately or together, to enhance the cleaning effect. When such nanoparticles are added to a liquid medium, and ultrasonic sound waves propagate therethrough, cavitation bubbles form producing high forces on contaminates which adhere to the object being cleaned. The nanoparticles are carried by microjets on the surface of the object, and further aid in disinfecting and sterilizing the objects surface.

18 Claims, 14 Drawing Sheets

(51) Int. Cl.
*A61C 17/028* (2006.01)
*A61C 19/06* (2006.01)
*A61L 2/025* (2006.01)
*B08B 3/12* (2006.01)

(52) U.S. Cl.
CPC ............ *A61C 19/063* (2013.01); *A61L 2/025* (2013.01); *B08B 3/12* (2013.01); *A61L 2202/24* (2013.01); *A61L 2400/12* (2013.01)

(56) References Cited

U.S. PATENT DOCUMENTS

| | | | |
|---|---|---|---|
| 7,189,350 B2 * | 3/2007 | Kanno | A61L 2/206 422/39 |
| 2005/0109368 A1 * | 5/2005 | Goodson | B06B 1/0611 134/1 |
| 2012/0077143 A1 | 3/2012 | Fougere | |
| 2013/0196286 A1 * | 8/2013 | Rutberg | A61C 17/024 433/217.1 |
| 2015/0037201 A1 * | 2/2015 | Armour | A61B 90/06 600/203 |
| 2015/0044632 A1 | 2/2015 | Sonendo | |
| 2015/0111169 A1 | 4/2015 | Yamamoto et al. | |
| 2016/0220459 A1 * | 8/2016 | Sokolov | A61Q 11/00 |

\* cited by examiner

ULTRASONIC CLEANING DEVICE

CROSS-REFERENCE TO RELATED APPLICATIONS

This application claims the benefit of U.S. Provisional Application No. 62/787,910 filed on Jan. 3, 2019, the contents of which are hereby incorporated by reference.

TECHNICAL FIELD

The disclosure generally relates to ultrasonic devices and particularly to ultrasonic disinfecting and sterilizing devices using nanoparticles.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section. Similarly, issues identified with respect to one or more approaches should not assume to have been recognized in any prior art on the basis of this section, unless otherwise indicated.

Hygiene has been an increasingly important part of human life, directly leading to a higher quality of living standard for billions worldwide. It is therefore no surprise that ecosystem industries, from toothbrush manufacturing, soaps, scrubs, mouthwash to medical dental device companies are all billion dollar industries.

Use of ultrasonic devices for hygiene is known in the art. For example AU2013268740 discloses a device and method for removing plaque using ultrasonic vibration thru a cleaning liquid. An ultrasonic oral cleaning device is disclosed in JP5786166B2 that ultrasonically cleans the oral cavity while pouring a cleaning liquid propagating ultrasonic waves as flowing water. The antimicrobial, bactericidal and disinfecting effects of various metals such as silver, copper, zinc, and titanium are well known in the art and have been well documented. Nanoparticle carriers may use ultrasonically generated microbubbles as described by Mullin et al., 2013. ("Nanoparticle delivery enhancement with acoustically activated microbubbles." IEEE transactions on ultrasonics, ferroelectrics, and frequency control, 60, 1,) as a means of drug and gene delivery which improves their efficacy and increases cellular and vascular permeability.

It is therefore apparent that it would be beneficial to improve methods of cleaning, disinfection, and sterilization of medical devices and apparatus.

BRIEF DESCRIPTION OF THE DRAWINGS

The subject matter of the disclosure is particularly pointed out and distinctly claimed in the claims at the conclusion of the specification. The foregoing and other objects, features, and advantages will be apparent from the following detailed description taken in conjunction with the accompanying drawings, of which:

DETAILED DESCRIPTION

Figure 1:
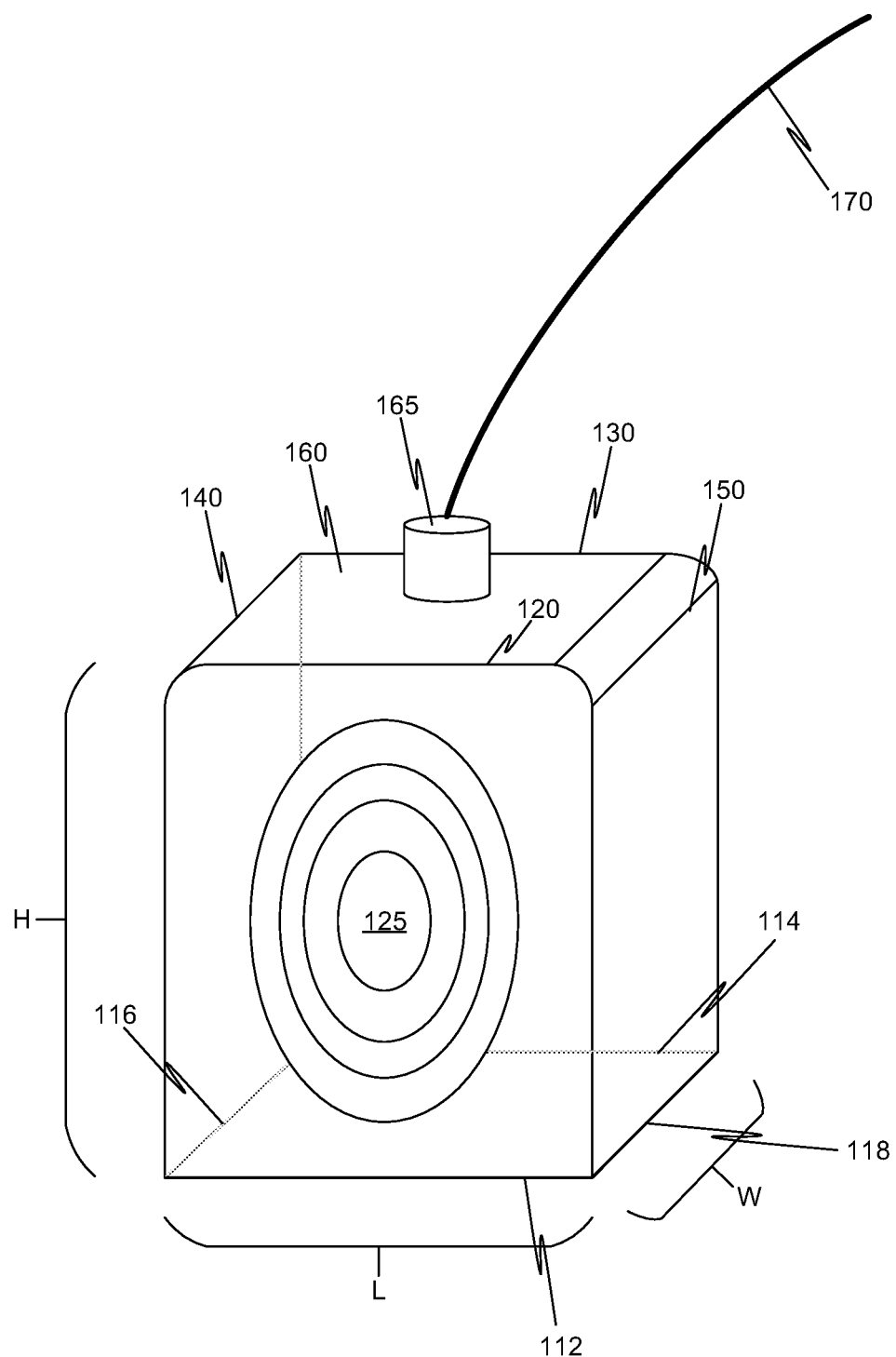
FIG. 1—is a schematic illustration of an ultrasonic cleansing dental device, implemented in accordance with an embodiment.

Below, exemplary embodiments will be described in detail with reference to accompanying drawings so as to be easily realized by a person having ordinary knowledge in the art. The exemplary embodiments may be embodied in various forms without being limited to the exemplary embodiments set forth herein. Descriptions of well-known parts are omitted for clarity, and like reference numerals refer to like elements throughout.

It is important to note that the embodiments disclosed herein are only examples of the many advantageous uses of the innovative teachings herein. In general, statements made in the specification of the present application do not necessarily limit any of the various claims. Moreover, some statements may apply to some inventive features but not to others. In general, unless otherwise indicated, singular elements may be in plural and vice versa with no loss of generality.

Ultrasonic cleaning methods may be enhanced by adding certain particles to a liquid through which ultrasonic waves travel through. Specifically, metal nitrites, metal carbides, and metal oxide particles may be used separately or together, to enhance the cleaning effect. When such nanoparticles are added to a liquid medium, and ultrasonic sound waves propagate therethrough, cavitation bubbles form producing high forces on contaminates which adhere to the object being cleaned. The nanoparticles are carried by microjets on the surface of the object, and further aid in disinfecting and sterilizing the object's surface.

FIG. 1 is a non-limiting exemplary schematic illustration of an ultrasonic cleansing dental device 100, implemented in accordance with an embodiment. The device 100 comprises a multi-faceted substantially hollow container, having at least one facet open and operative for covering one or more teeth. In this embodiment, the bottom facet 110 is open, and is defined by a front edge 112, a back edge 114, a left edge 116 and a right edge 118. The edges may be of material having higher elasticity and/or friction, which can increase the hold the device 100 has on the one or more teeth it is placed on. For example, silicone may be used to substantially create a seal between the hollow container and a tooth. Silicone is a material which has high adherence and the device 100 would therefore be more likely to stay in place, rather than using, say, a rigid plastic. The device further includes a front facet 120, a back facet 130, a left facet 140, a right facet 150, and a top facet 160. An ultrasonic transducer 125 is coupled with the front facet 120. The transducer 125 may be coupled on an external portion of the front facet 120, or on an internal portion of the front facet 120. Coupling the transducer 125 on the internal portion of the front facet is beneficial since it allows direct contact between the transducer 215 and the liquid medium. The front facet 120 has a height 'H' which should be high enough so that the edges of the bottom facet 110 is able to touch the gums beneath the tooth. The side facets 140 and 150 have a width 'W' which are at least as wide as a tooth. The width may be to accommodate, for example, a molar, an incisor, and the like. In some embodiments, a first side may have a first width, and a second side have a second width, which can be beneficial for example when containing multiple teeth such as a premolar and an adjacent cuspid. The front facet 120 has a length 'L' which is long enough to include at least one tooth in the hollow container. While these measurements are typical to cubic geometries such as the one in this exemplary embodiment, it should be evident to those skilled in the art that other geometric container shapes may be used which could differ substantially geometrically (such as a cylinder, spherical cap, etc.) but pertain the same functionality of containing one or more teeth for ultrasonic cleansing. The top facet 160 includes a valve 165, into which a conduit 170 may be coupled. In an embodiment, the valve 165 may allow fluid to flow only into the device 100. In some embodiments, the valve 165 may be located on any facet other than the bottom facet. In certain embodiments, a plurality of valves may be used, on one or more facets. In certain embodiments, a mouthguard piece may be used, such as mouthguard 450 of FIG. 4B. The mouthguard structure may include one or more embedded ultrasonic transducers, such as the transducer 125, which may be placed on a front facet, back facet, or a combination thereof, of the mouthguard.

Figure 2A:
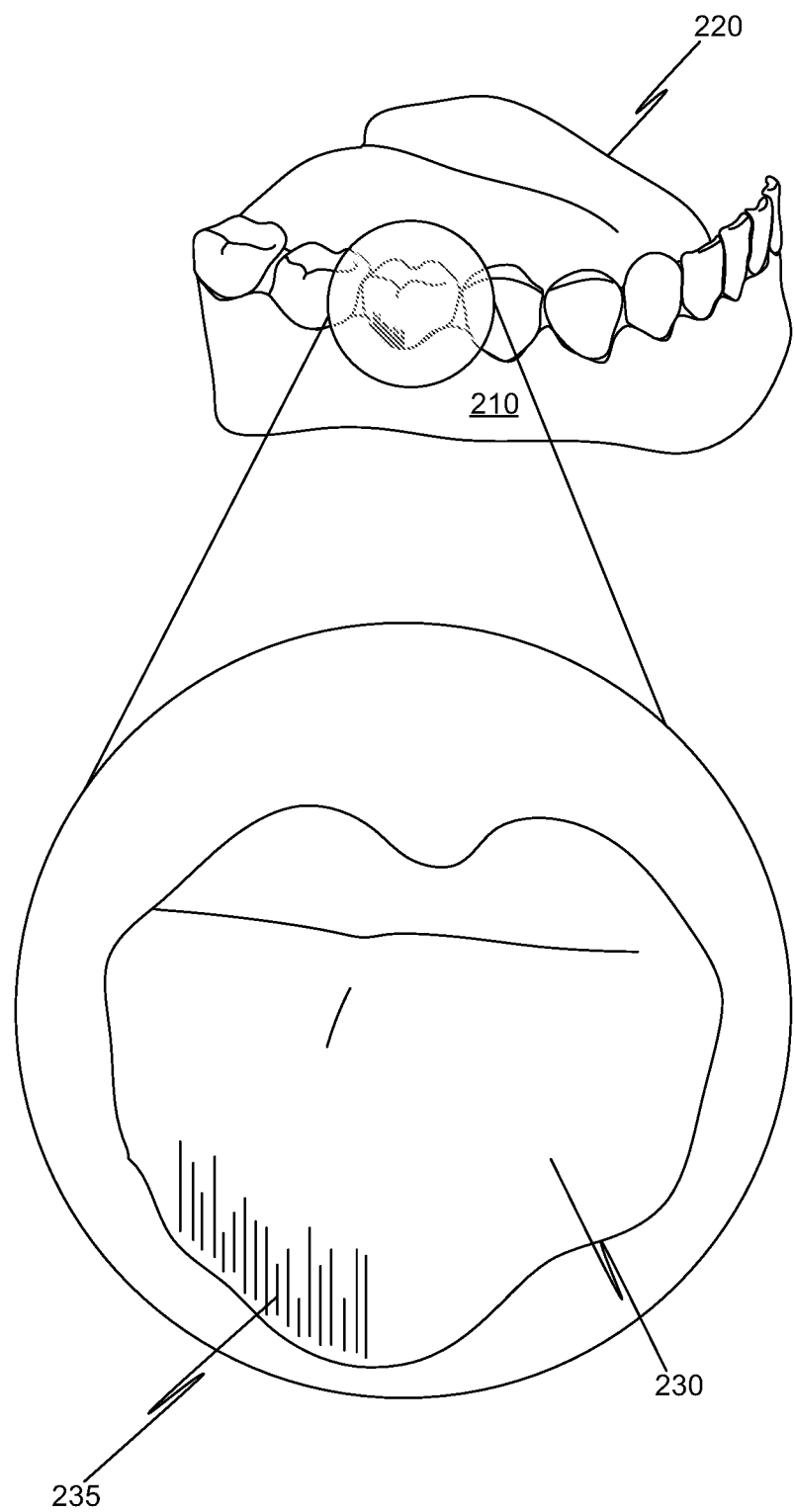
FIG. 2A—is a schematic illustration of a bottom right portion of a human mouth, in accordance with an embodiment.

FIG. 2A is a non-limiting exemplary schematic illustration of a bottom right portion of a human mouth, in accordance with an embodiment. The mouth includes a plurality of teeth attached to a gum 210, and in contact with a tongue 220. The first molar 230, includes a portion with plaque buildup 235. Plaque is comprised of bacteria and food debris, which is easily left undisturbed in areas which are hard to reach, such as between individual teeth. Periodontal bacteria which are naturally present in the oral cavity can multiply in an unhealthy manner under such conditions, leading to a disease known as periodontitis. This may produce inflammation of the gums, which can destroy the jaw bone, and cause loose teeth, among other side effects. However, by eliminating the plaque on teeth the disease can be altogether prevented. Even in cases where the disease has progressed, removal of the plaque, and subsequent tartar buildup, is desirable.

Figure 2B:
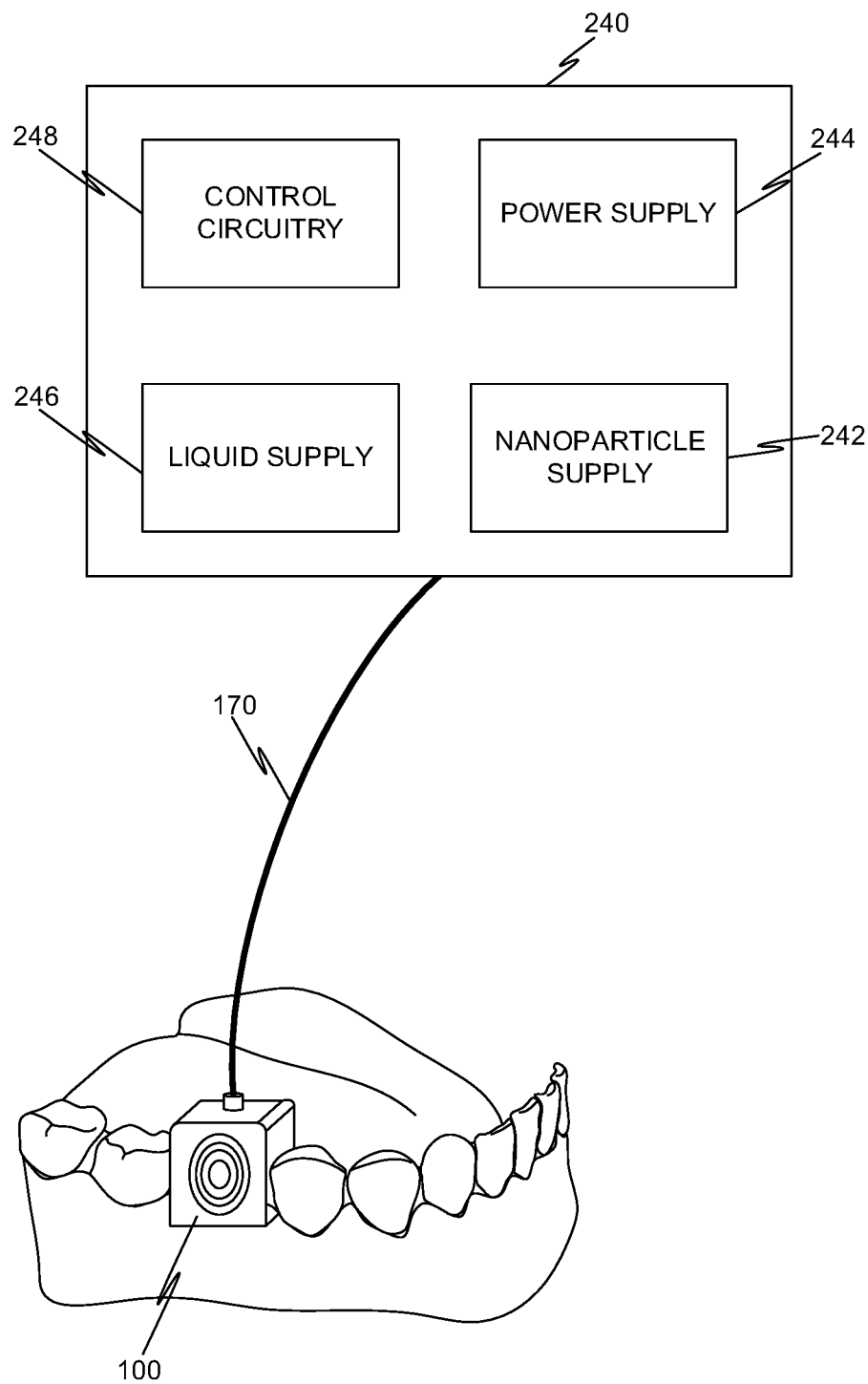
FIG. 2B—is a schematic illustration of an ultrasonic cleansing dental device operating on a first molar, implemented in accordance with an embodiment.

FIG. 2B is a non-limiting exemplary schematic illustration of an ultrasonic cleansing dental device operating on a first molar, implemented in accordance with an embodiment. The dental device 100 encloses the first molar 230 of FIG. 2A. In a preferred embodiment, the device creates a seal between the bottom edges of the device and the gum, or a bottom portion of the tooth. A conduit 170 is coupled with the dental device 100 and a controller 240. The controller 240 includes a nanoparticle supply 242, a power supply 244, a liquid supply 246, and a control circuitry 248. In an embodiment the nanoparticle supply 242 and liquid supply 246 may be a single supply, such that the nanoparticles are already suspended in the liquid which is delivered into the dental device 100 via the conduit 170. The liquid may hold therein a suspension of insoluble nanoparticles. A nanoparticle may be between 1 and 200 nanometers in size. For the purpose of this disclosure, in certain embodiments micron-sized particles may also be used, however they may not have the desired effect. Exemplary nanoparticles may be metal oxides, metal nitrides and metal carbides. Metal oxides such as Silicon Dioxide, Aluminum dioxide, Magnesium Oxide, Samarium oxide, Titanium Dioxide, and Zinc Oxide. Metal nitrides such as Silicon Nitride and Titanium Nitride. Metal carbides, such as Silicon Carbide, Titanium Carbide, and Tungsten Carbide. In certain embodiments, diamond nanoparticles may be used. In certain embodiments, the ratio between liquid and nanoparticles held in a suspension therein is between 10,000 and 100,000 parts liquid medium to 1 part nanoparticles. In another embodiment the ratio may be between 1,000-1,000,000 parts fluid medium to 1 part nanoparticle. In some embodiments, the nanoparticles may have a morphology which includes one or more sharp shapes. A sharp shape for the purpose of this disclosure is a shape which includes a surface feature that is capable of piercing or otherwise destroying infectious agents (pathogens), such as membrane of a bacteria, or virions. For example, rods, or stars are such shapes. The power supply supplies power to various electronic and mechanical elements of the controller 240, such as a pump (not shown) which is used to regulate flow from the liquid supply 246 through the conduit 170 to the device 100, and the ultrasonic transducer of the device 100. Control circuitry 248 may be used to regulate the power supply 244, or the nanoparticle supply 242 and liquid supply 246 to change the type of nanoparticles (if various particles are used), the ration between the liquid and nanoparticles, etc. The controller 240 supplies a constant stream of liquid with suspended nanoparticles to the device 100, inducing the generation of cavities that implode via micro-jets of the liquid that carry with them the nanoparticles which bombard the surface of the tooth. This may result in full or partial removing of coatings like plaque and pathogens. Depending on the type of nanoparticles used, this may further cause disinfection or sterilization. The dental device 100 may be used before, after, and during dental procedures where disinfection is required or may aid in the procedure, for example. In certain embodiments the dental device 100 may have the shape of a mouthguard for a plurality of teeth.

Figure 3:
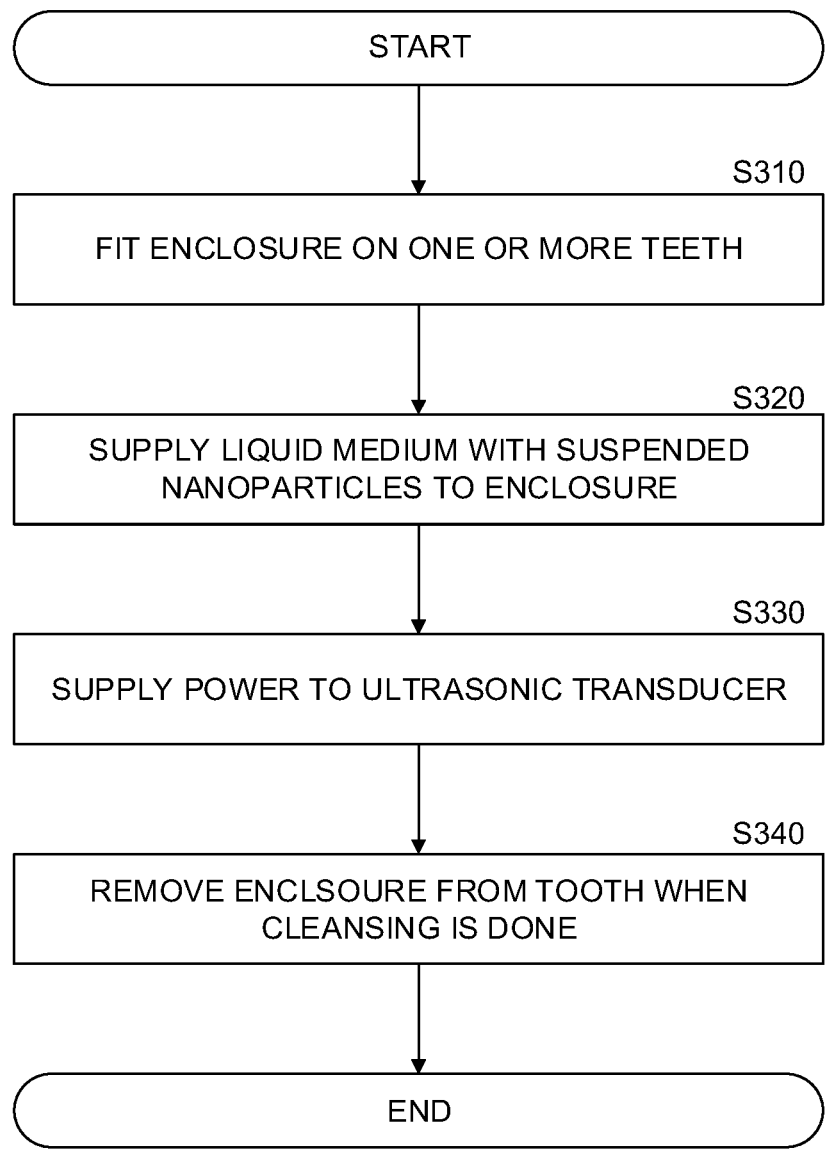
FIG. 3—is a method for providing ultrasonic cleansing to one or more teeth, implemented in accordance with an embodiment.

FIG. 3 is a method for providing ultrasonic cleansing to one or more teeth, implemented in accordance with an embodiment.

In S310 an enclosure is fitted around one or more teeth, the enclosure including a valve for coupling with a conduit and an ultrasonic transducer.

In S320 a liquid medium containing suspended nanoparticles is supplied to the enclosure from the conduit via the valve. In some embodiments, the valve is unidirectional. In certain embodiments the liquid medium may be provided at a regulated flow and pressure. In some embodiments, the conduit may supply a first liquid with a first nanoparticle suspension, and then supply a second liquid with a second nanoparticle suspension. The first and second suspensions may differ in nanoparticle type, nanoparticle size, ratio of nanoparticles to liquid, liquid type, liquid viscosity, combinations thereof, and the like.

In S330 the ultrasonic transducer is supplied with power and generates ultrasonic waves, which are carried by the liquid medium. This has the effect of cleaning, disinfecting or sterilizing the tooth surface with which the liquid medium comes to contact with, and depending on the nanoparticle type and shape, different levels of cleanliness may be achieved.

In S340 the enclosure is removed from the tooth, after the liquid medium supply is turned off and the ultrasonic transducer is inactive.

Figure 4A:
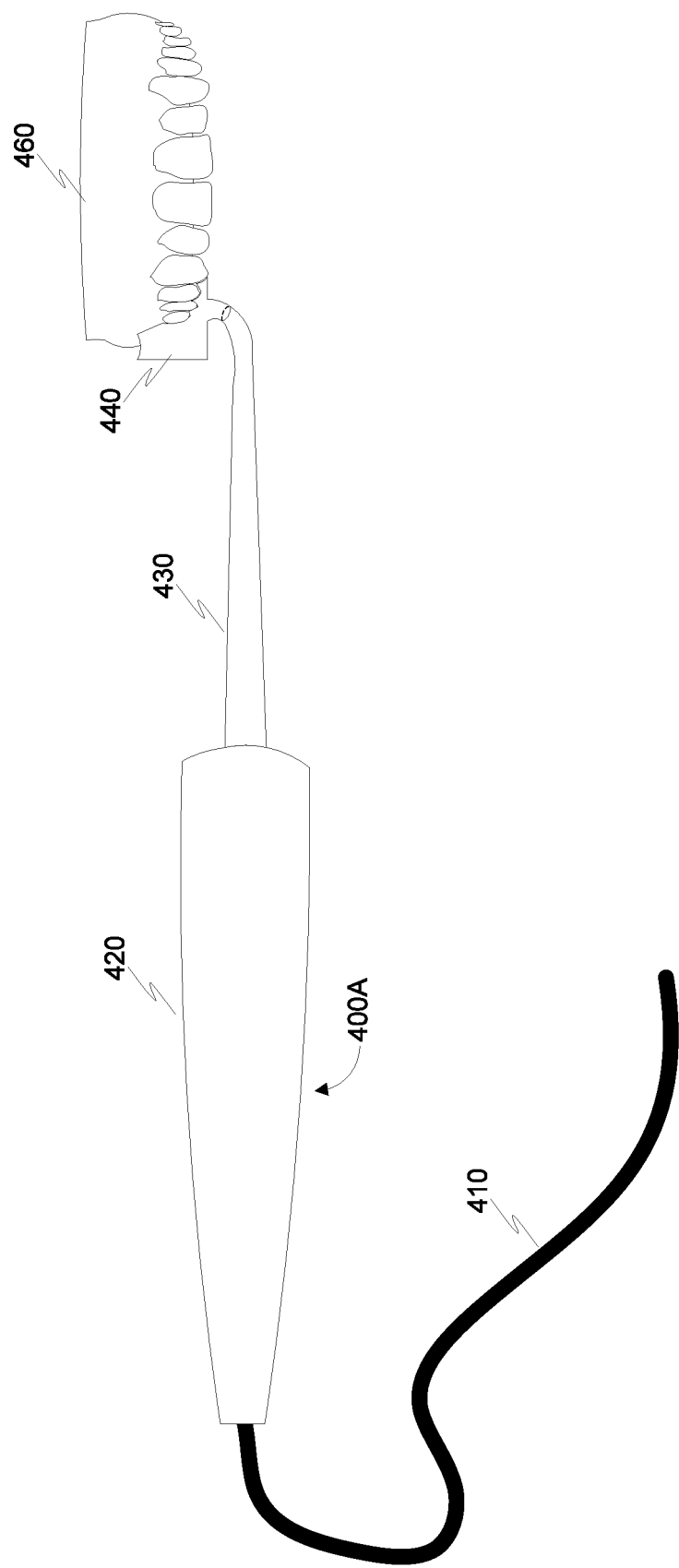
FIG. 4A—is a schematic illustration of an ultrasonic scaler device with nanoparticle cleansing capabilities, implemented in accordance with an embodiment.

FIG. 4A is a schematic illustration of an ultrasonic scaler device with nanoparticle cleansing capabilities, implemented in accordance with an embodiment. An ultrasonic scaler 400A includes an input cord 410, a main body 420, an extended body portion 430 and tooth container 440. In some embodiments the tooth container 440 may be adapted to fit one or more teeth. In certain embodiments the tooth container 440 may be decoupled from the extended body portion 430 such that a liquid spray is extruded from a nozzle of the extended body portion 430 directly onto a dental surface. An input cord 410 includes therein a fluid supply hose, and at least a power line to supply power to at least an ultrasonic transducer contained inside the main body 420. The main body 420 may include therein electronic circuitry for controlling functionality of the scaler, and an ultrasonic transducer. The ultrasonic scaler is explained in more detail in FIG. 5 below. The main body 420 is coupled with an extended body portion 430. The extended body portion 430 may include therein a probe coupled with the ultrasonic transducer, which is in contact with the fluid supplied by the input cord 410 to generate the effects described above.

Figure 4B:
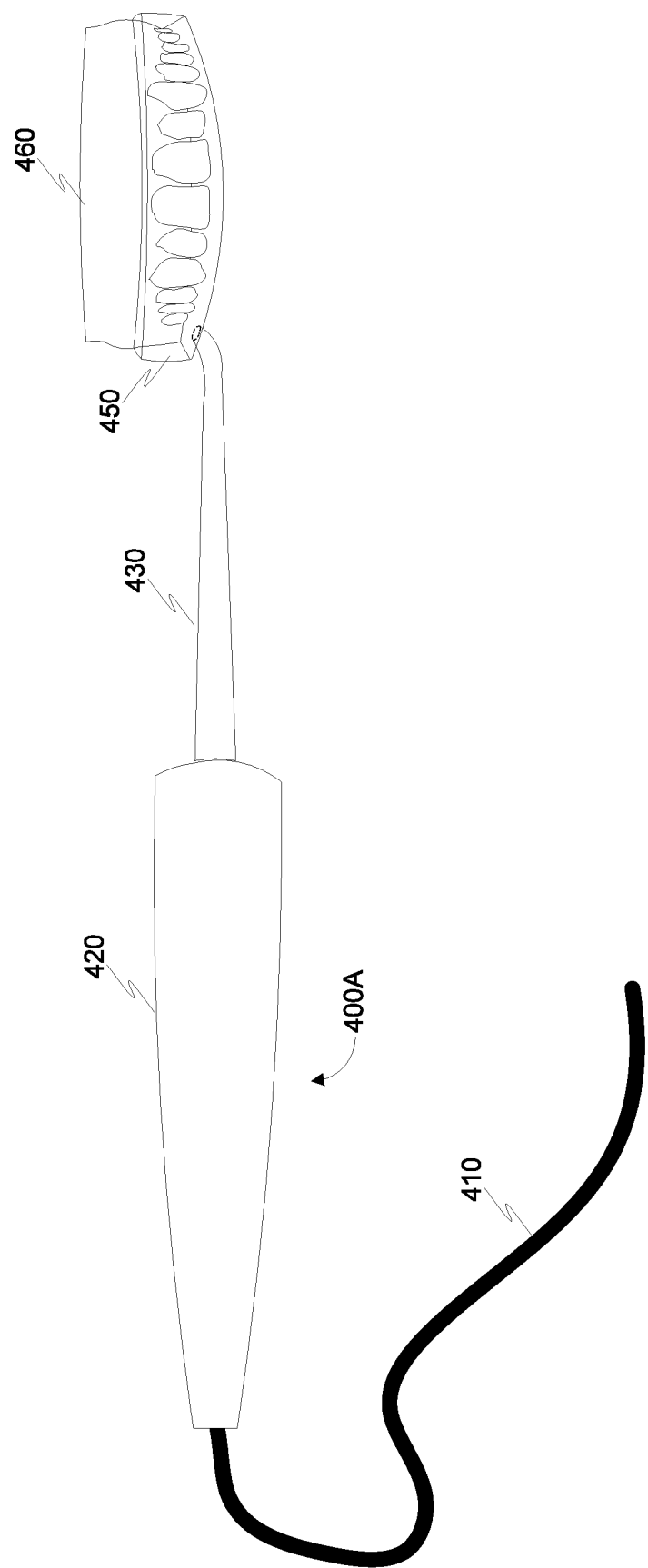
FIG. 4B—is a schematic illustration of an ultrasonic scaler device with nanoparticle cleansing capabilities, implemented in accordance with another embodiment.

FIG. 4B is a schematic illustration of an ultrasonic scaler device with nanoparticle cleansing capabilities, implemented in accordance with another embodiment. An ultrasonic scaler 400B includes an input cord 410, a main body 420, an extended body portion 430 and a mouth guard 450. While one or more teeth may be contained by the tooth container 440 of FIG. 4A, a mouth guard 450 may be coupled with the extended body portion 430 which may contain an entire set of upper teeth, lower teeth, or both. A mouthguard 450 may be easier to operate for a non-skilled operator, and may be operated by a user at their home. This is advantageous as it would allow non-skilled users to achieve cleansing results otherwise reserved for professionals. Meanwhile, a container operative for one or more teeth may use less fluid and nanoparticle powder due to being smaller in size, and therefore reduces waste in treatments, for example such as those performed by a dental professional. In certain embodiments, the mouthguard 450 and or the tooth container 440 may be formed of an elastomer material, such as silicone rubber, for example. An elastomer may adhere better to the gums 460, creating a seal which ensures that the dental surfaces intended for cleaning are all immersed in nanoparticle solution. This in turn ensures a deeper level of cleaning. In some embodiments the tooth container 440 or mouthguard 450 may contain a first perforation to couple with the extended body portion 430, and a second perforation (not shown) to allow excess fluid to exit the enclosure.

Figure 5:
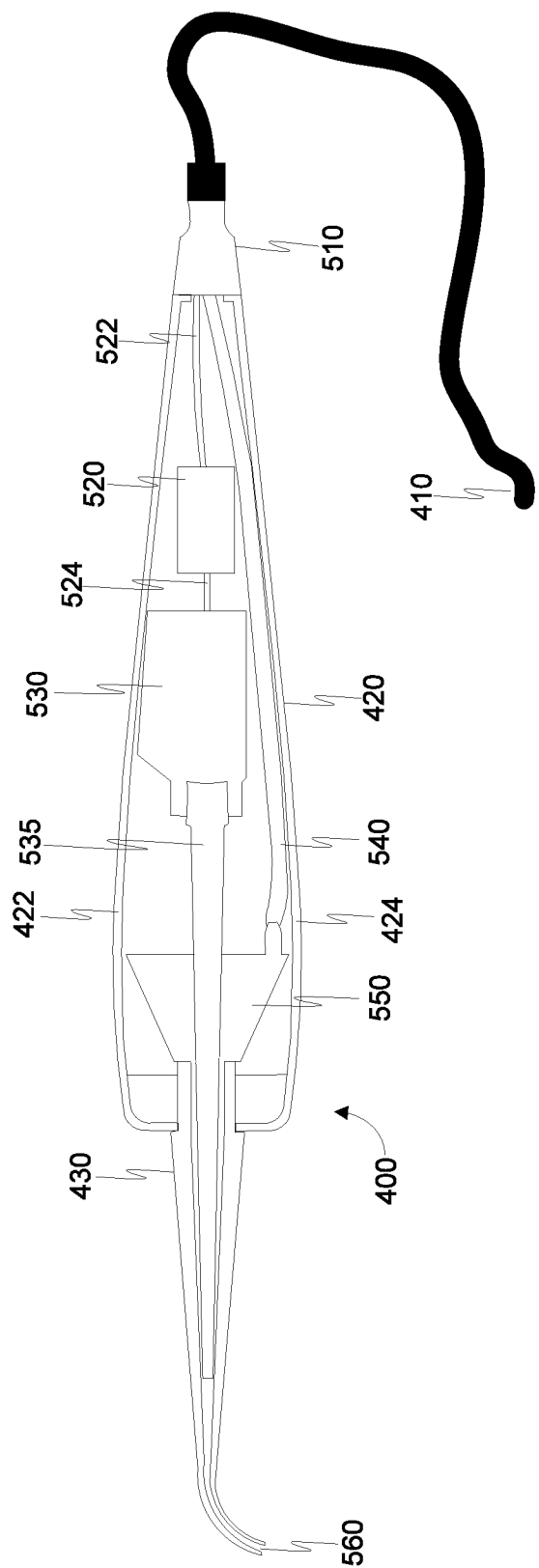
FIG. 5—is a longitudinal cross section view of an ultrasonic scaler device with nanoparticle cleansing capabilities, implemented in accordance with an embodiment.

FIG. 5 is a longitudinal cross section view of an ultrasonic scaler device with nanoparticle cleansing capabilities, implemented in accordance with an embodiment. An ultrasonic scaler device 400 includes an inlet 510 for coupling with a supply cord 410. The supply cord 410 in this embodiment includes both a power supply 522 and a fluid supply 540. In this embodiment the fluid supply 540 supplies the device with a nanoparticle solution from the fluid supply 540, such as that which is received from the controller 240 of FIG. 2. The inlet 510 is coupled with a main body 420 of the device 400. The main body includes a top wall portion 422 and bottom wall portion 424 creating a hollow substantially tubular volume in between. Within the main body 420 the power supply 522 is coupled with an electronic circuit 520, which is coupled via an electric supply 524 to an ultrasonic generator 530. The ultrasonic generator 530 is operative for generating ultrasonic waves to be delivered via an ultrasonic transducing rod 535. The transducing rod 535 may be comprised of a material conducting ultrasonic waves. The transducing rod 535 extrudes from the main body 420 into an extended body portion 430, through a cavity 550. The cavity 550 is a hollow portion within the main body 420, into which fluid from the fluid supply 540 flows. The fluid comes in contact with the transducing rod 535 in the cavity 550. The cavity 550 may have a cross section tapering towards the extended portion 430, and couples with a hollow portion of the extended portion 430 so that fluid present in the cavity 550 can be released at a higher pressure through the extended portion 430, and from an outlet 560 of the extended portion 430. The transducing rod 535 extends from the cavity 550 into the extended portion 430, all the while in contact with the fluid supplied from the fluid supply 540. The extended portion may likewise taper so that a smaller cross section is formed as fluid moves away from the cavity 550, thus increasing pressure and giving the fluid a higher kinetic energy. This may assist in removing debris from the dental surface by transferring the kinetic energy from the nanoparticles and fluid to the debris, upon impact. The scaler device 400 may be coupled with an enclosure, such as mouthguard 450, or used without, so that the outlet 560 is directed towards an area of the oral cavity and the liquid with nanoparticle suspension is jettisoned towards the area. In some embodiments the scaler device 400 may be operative for coupling with an enclosure, in others it may be operative to operate without an enclosure, and in yet other embodiments the scaler device 400 may be operative for both.

Figure 6:
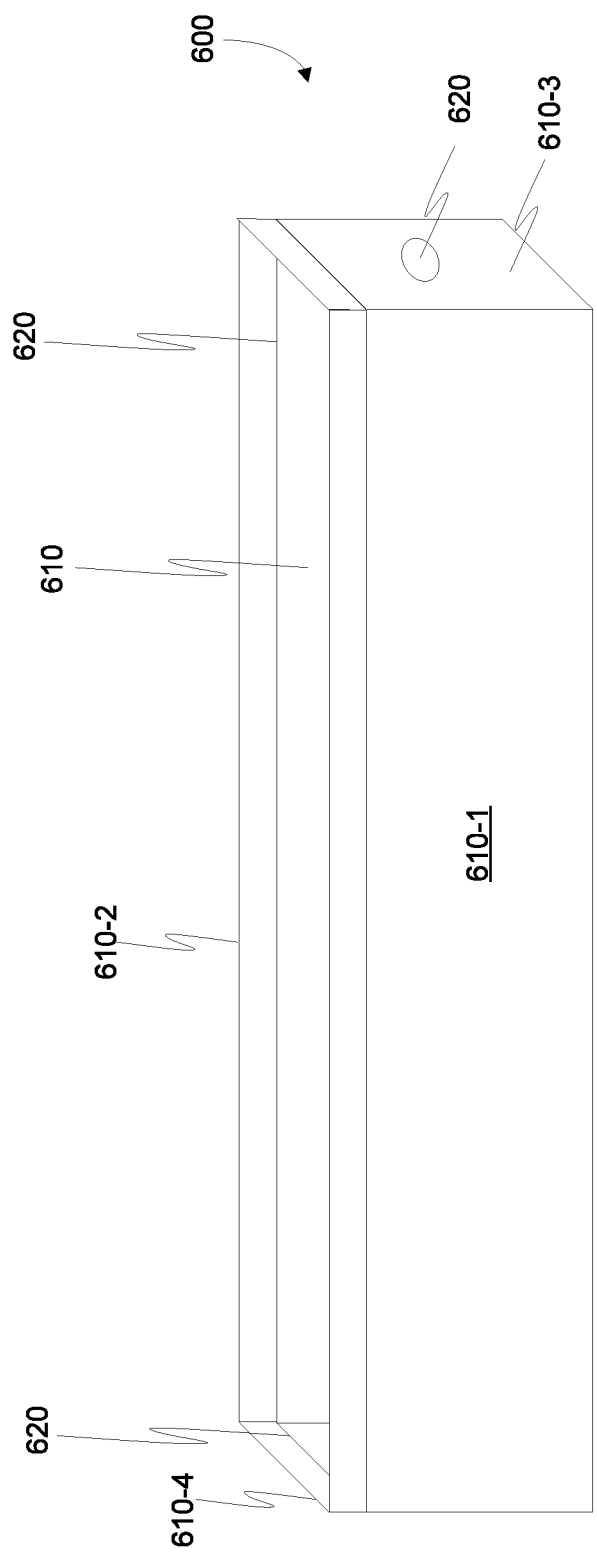
FIG. 6—is a front top right isometric view of an ultrasonic bath for sterilizing and/or disinfecting equipment, implemented in accordance with an embodiment.

FIG. 6 is a front top right isometric view of an ultrasonic bath for sterilizing and/or disinfecting equipment, implemented in accordance with an embodiment. the ultrasonic bath may be used for disinfecting and/or sterilizing medical equipment, such as the dental device discussed in more detail above. The ultrasonic bath 600 includes a container 610, which in this embodiment includes four walls—a front wall 610-1, a back wall 610-2, a right wall 610-3 and a left wall 610-4. The container 610 is impermeable to liquid mediums, such as water. A liquid medium may fill the container 610 up to a level, which may be marked for example by a circumferential line 620. The liquid medium may hold therein a suspension of insoluble nanoparticles. A nanoparticle may be between 1 and 100 nanometers in size. For the purpose of this disclosure, in certain embodiments micron-sized particles may also be used, however they may not have the desired effect. Examples of nanoparticles may be metal oxides, metal nitrides and metal carbides. Metal oxides such as Silicon Dioxide, Aluminum dioxide, Magnesium Oxide, Samarium oxide, Titanium Dioxide, and Zinc Oxide. Metal nitrides such as Silicon Nitride and Titanium Nitride. Metal carbides, such as Silicon Carbide, Titanium Carbide, and Tungsten Carbide. Some of these, such as Zinc Oxide and Titanium Dioxide further have photocatalytic properties which may include desired properties when disinfecting or sterilizing certain objects sensitive to electrical charges induced by intense light further using photosensitive elements. In certain embodiments, the ratio between liquid medium and nanoparticles held in a suspension therein is between 10,000 and 100,000 parts liquid medium to 1 part nanoparticles. The container 610 further includes an ultrasonic transducer (not shown, which may be affixed on an outer surface) which is connected via an interface 630 to a controller (described in more detail below), and in some embodiments may include a removable wire rack (or, in another embodiment, a wired metal basket) upon which a medical device may be placed for sterilization, such that the rack fully supports a device from touching or making contact with the container, while both the device and the rack are entirely submerged in the liquid medium. In some embodiments, the nanoparticles may have a morphology which includes one or more sharp shapes. A sharp shape for the purpose of this disclosure is a shape which includes a surface feature that is capable of piercing or otherwise destroying infectious agents (pathogens), such as membrane of a bacteria, or virions. For example rods, or stars are such shapes.

Figure 7:
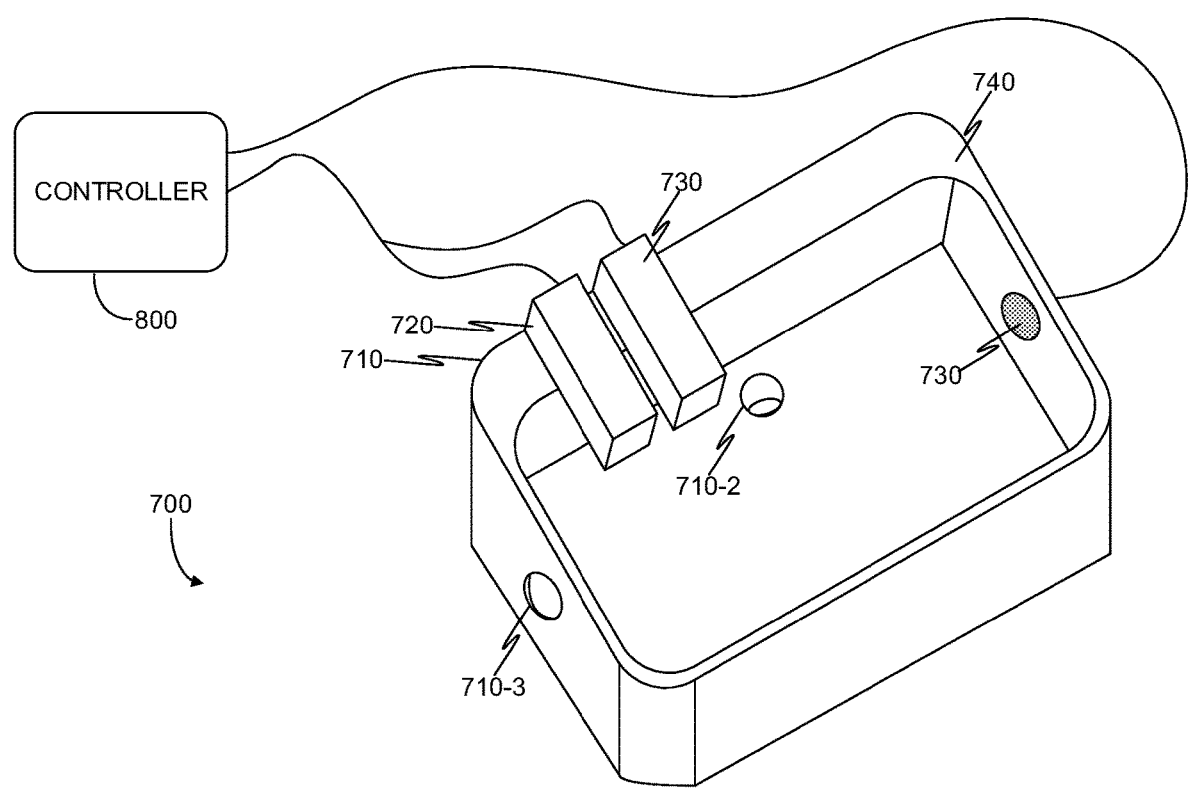
FIG. 7—is a top front right isometric view of an ultrasonic bath for sterilizing and/or disinfecting equipment, implemented in accordance with another embodiment.

FIG. 7 is a top front right isometric view of an ultrasonic bath for sterilizing and/or disinfecting equipment, implemented in accordance with another embodiment. Equipment may be medical devices such as the device of FIG. 1, toys, pacifiers, baby bottles, toothbrushes, and the like. An ultrasonic (US) bath system 700 includes a container 710, a first dispenser 720, a second dispenser 730 and a control unit 800. The container includes an ultrasonic transducing element 710-1, a drain 710-2, and an intake 710-3 for filling the container with liquid. The liquid may be water-based or ethanol-based, the latter which may be useful for medical devices with electronics or batteries which could be damaged by the conductive properties of water. The US transducing element 710-1 is operative for generating US waves. In an embodiment, the US transducing element 710-1 may be a transmitter, or a transceiver of US waves. The US transducing element 710-1 applies US waves to the liquid medium in the container 710 to agitate the nanoparticles suspended therein. Methods and specifications of agitating nanoparticles suspended in an aqueous medium are discussed in more detail in U.S. patent application Ser. No. 16/105,055, the contents of which are incorporated by reference herein, having a common inventor. In this embodiment the US bath system 700 includes a first dispenser 720 and a second dispenser 730, each of which is operable for disposing into the container a measured amount of nanoparticles, such that a first type of nanoparticle mixture is present in the first dispenser, and a second type of nanoparticle mixture is present in the second dispenser. In some embodiments, a single dispenser, or a plurality of dispensers greater than two may be used. A dispenser may contain therein a powder mix of numerous types of nanoparticles. For example, the first dispenser 720 may include Silicon Dioxide and Magnesium Oxide at a predetermined ratio, while the second dispenser 730 includes Zinc Oxide. The dispensers may be positioned on the top panel 740 of the container, such that a portion of the dispenser is supported by the top panel 740 (or any of the sidewalls of the container, in an embodiment), and at least a portion of the dispenser, through which the nanoparticle powder is extruded, is positioned over the container 710. In an embodiment, the intake 710-3 is operative for accepting a conduit (such as a pipe) which provides the liquid medium. The drain 710-2 may be in a closed position which does not allow liquid medium to exit the container, an open position which allows the liquid medium to exit the container, or in some embodiments, one or more positions in between, whereby the drain is partially open, allowing a limited flow of liquid medium to exit the container. The controller 800 is communicatively coupled with the first dispenser 720, the second dispenser 730, and the US transducing element 710-1. The controller, which is discussed in more detail in FIG. 8 below, is operative for controlling the dispensing action from one or more dispensers, for controlling the operation of the US transducing element 710-1, and in some embodiments, for controlling the position of the drain (closed, open, partially open), and in yet other embodiments for controlling the intake 710-3. The controller may monitor operation and control of the above. For example, the controller may apply a voltage to an actuator to position the drain in the open position, and do so until the liquid medium in the container has been removed. The controller may then apply a second voltage to the actuator to position the drain in the closed position. Once the controller determines the drain is in the closed position, the controller may apply a voltage to an actuator on the intake 710-3, which causes the container to fill with liquid. The controller may keep the intake 710-3 in an open position for a predetermined amount of time, an amount of time specified by an operator, or for an amount of time corresponding to a volume of liquid filling the container 710. Accordingly, the controller may determine a ratio between the liquid medium which was filled in the container, and a corresponding amount of nanoparticle powder to be dispensed by a dispenser. The controller may then configure a dispenser, such as first dispenser 720 to dispense the determined amount of nanoparticle powder into the liquid medium. Automating this process has an advantage of receiving a consistent ratio of liquid medium to suspended nanoparticles, which ensures operation at a predetermined optimal level. In certain embodiments, additional chemicals may be added to the liquid medium, such as chlorine, copper, antibiotics, silver particles, and the like. For example, silver sulfadiazine may be added, which has antibacterial properties which may aid in disinfecting and/or sterilizing equipment. In some examples, the controller may configure the US bath system 200 to go through one or more cycles, each with a different solution. For example, a first solution may include a first liquid medium and a first type of nanoparticle, followed by draining the liquid solution, refilling the container and adding a second type of nanoparticle together with an antibiotic, followed by draining the second liquid solution, refilling the container with liquid, and finally draining the container to remove the disinfected/sterilized object.

Figure 8:
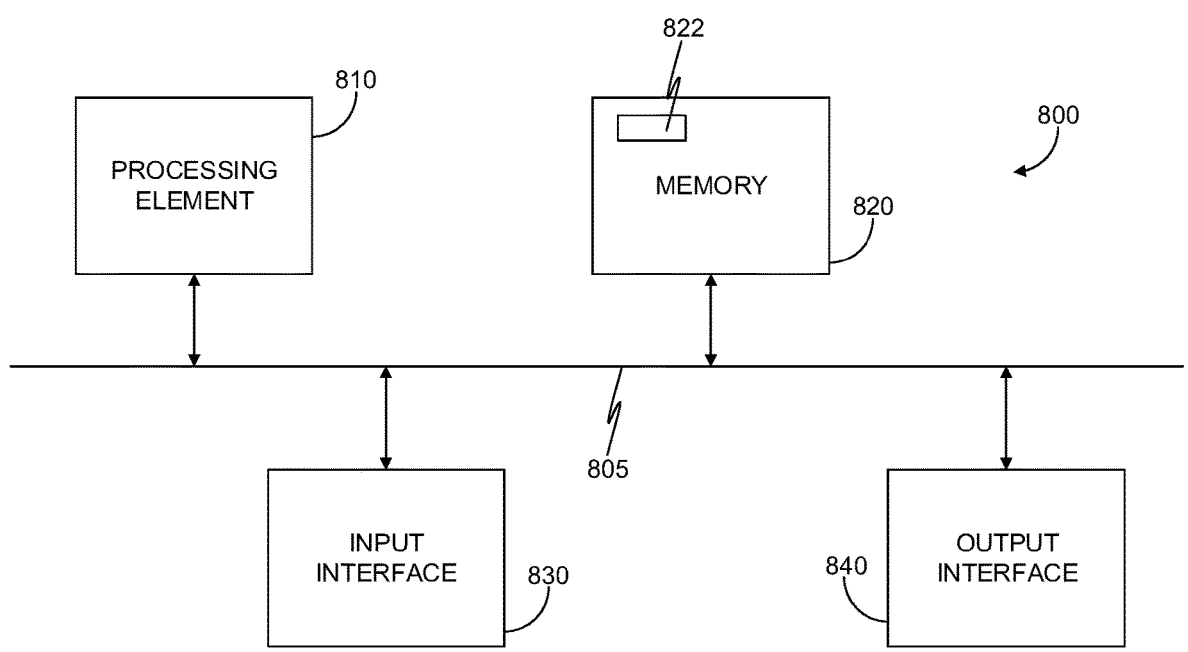
FIG. 8—is a schematic illustration of a controller for an ultrasonic bath system, implemented according to an embodiment.

FIG. 8 is an exemplary and non-limiting schematic illustration of a controller 800 for an ultrasonic bath system, implemented according to an embodiment. The controller 800 includes at least one processing element 810, for example, a central processing unit (CPU). In an embodiment, the processing element 810 may be, or be a component of, a larger processing unit implemented with one or more processors. The one or more processors may be implemented with any combination of general-purpose microprocessors, microcontrollers, digital signal processors (DSPs), field programmable gate array (FPGAs), programmable logic devices (PLDs), controllers, state machines, gated logic, discrete hardware components, dedicated hardware finite state machines, or any other suitable entities that can perform calculations or other manipulations of information. The processing element 810 is coupled via a bus 805 to a memory 820. The memory 820 may include a memory portion 822 that contains instructions that when executed by the processing element 810 performs the method described in more detail herein. The memory 820 may be further used as a working scratch pad for the processing element 810, a temporary storage, and others, as the case may be. The memory 820 may be a volatile memory such as, but not limited to random access memory (RAM), or non-volatile memory (NVM), such as, but not limited to, flash memory. The processing element 810 may be coupled to an input interface 830. The input interface is operative for receiving inputs for example from one or more sensors communicatively attached thereto. A sensor may be an image sensor, a temperature sensor, and ultrasonic receiver, and the like. An image sensor may be used to determine the level of liquid relative to the internal height of the container walls. A temperature sensor may be used to determine the temperature of the liquid medium in the container, and an US receiver may be used to determine the frequency emitted by an US transmitter. The processing element 810 may be further coupled with an output interface 840. The output interface 840 may include an interface for controlling actuators, for example, which may physically change the state of an intake or drain, or cause an US transducer to begin operation at a determined frequency and at a power level (measured in watts per liter) which is specified by the controller. In an embodiment, the controller 800 may further include a power controller, for receiving power from an electric grid source, and converting at least a portion of that power to an US transmitter coupled thereto. In some embodiments, the controller 800 may further include a network interface controller (NIC, not shown) for connecting the controller 800 to a network, and allowing the controller to receive instructions from a user device (such as a laptop computer, tablet, and the like) to operate, or specify operating parameters for, the US bath system. The instructions may be received over a network. In an embodiment, the network may be configured to provide connectivity of various sorts, as may be necessary, including but not limited to, wired and/or wireless connectivity, including, for example, local area network (LAN), wide area network (WAN), metro area network (MAN), worldwide web (WWW), Internet, and any combination thereof, as well as cellular connectivity. The processing element 810 and/or the memory 820 may also include machine-readable media for storing software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the one or more processors, cause the processing system to perform the various functions described in further detail herein.

Figure 9:
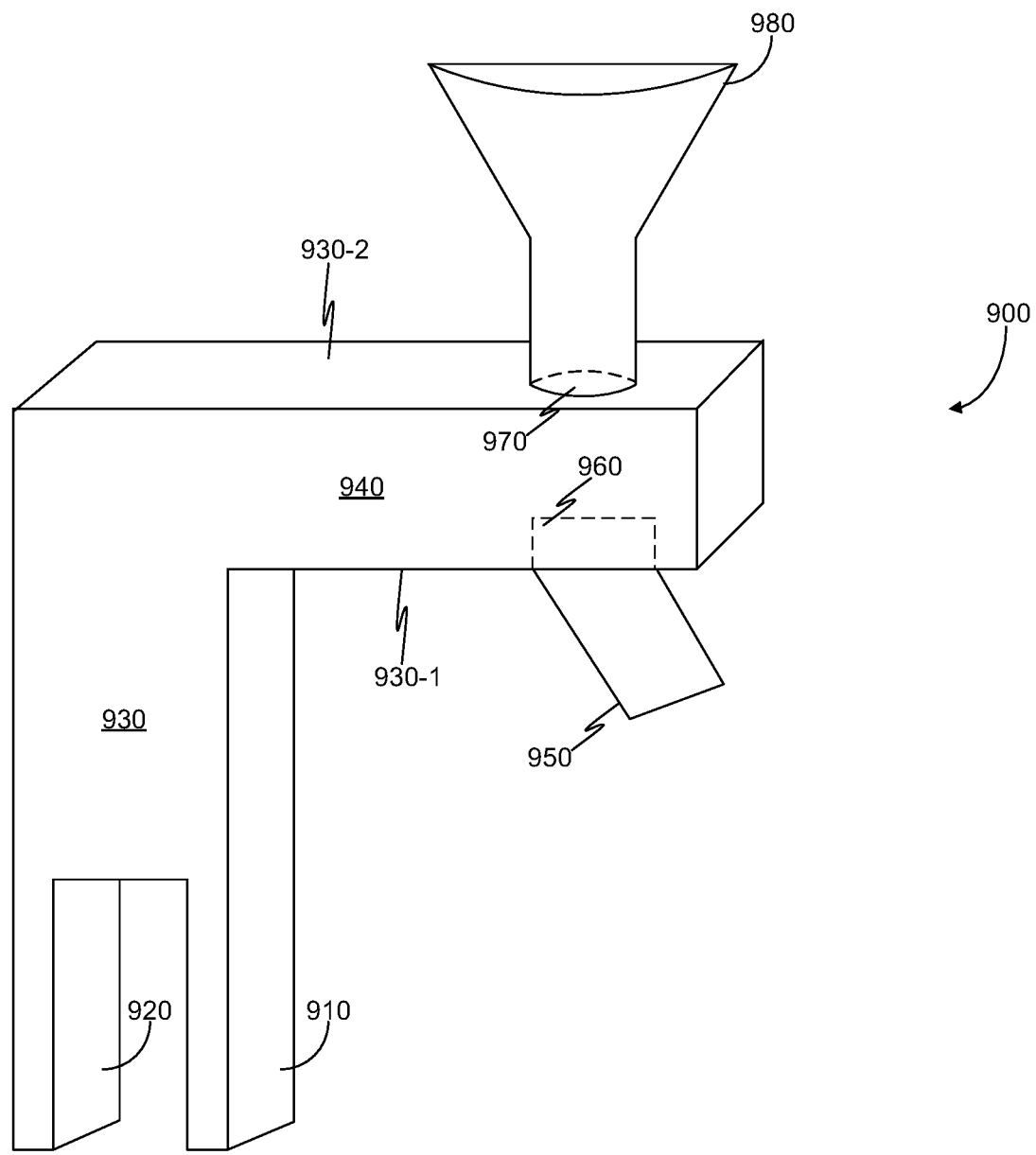
FIG. 9—is a schematic illustration of a left-side top front view of a nanoparticle powder dispenser, implemented in accordance with an embodiment.

FIG. 9 is a schematic illustration of a left-side top front view of a nanoparticle powder dispenser 900, implemented in accordance with an embodiment. A dispenser 900 includes a first leg 910 and a second leg 920, extruding from a body 930, which may be hollow in some embodiments, full, or a combination thereof. The body 930 is connected to a substantially orthogonal neck portion 940 which is at least partially hollow to allow for storing therein nanoparticle powders, or other chemicals used in an US bath system such as the one described above. The first leg 910 and second leg 920 are operative for clamping onto a sidewall of an US bath system container, such as container 710 of FIG. 7. The neck portion 900 extrudes substantially orthogonally from the body 930 such that a door 950, covering an opening 960 on the bottom 930-1 of the neck, is situated over the container, so that when the door is in an open position, exposing the opening 960 on the bottom 930-1 of the neck 930, a predetermined amount of nanoparticle powder is able to exit the dispenser in order for it to be added to a solution prepared with the liquid in the container. The door 950 may be coupled with an actuator which controls the door position. The actuator (not shown) may be communicatively coupled with a controller (such as controller 800 of FIG. 8) to operate the position of the door (i.e. when the door should be open, how much it should open, and for what period of time). In an embodiment, the dispenser 900 includes a second opening 970 on the top 930-2 of the neck. The second opening 970 is operative for receiving therein nanoparticle powder, allowing to fill the hollow portion of the neck 930. In an embodiment, the opening 970 is operative for coupling with a funnel 980, through which it is easier to fill the dispenser with chemicals.

Figure 10:
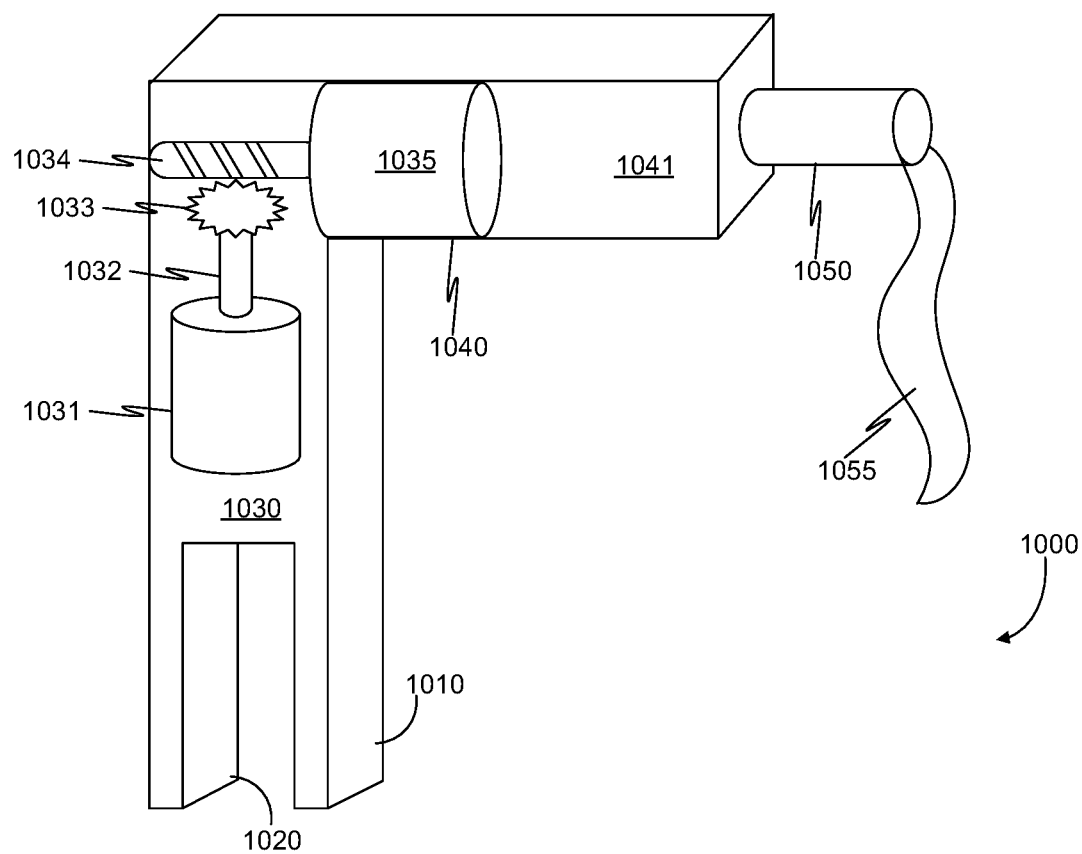
FIG. 10—is a schematic illustration of a left-side top front view of a nanoparticle fluid dispenser, implemented in accordance with an embodiment.

FIG. 10 is a schematic illustration of a left-side top front view of a nanoparticle fluid dispenser, implemented in accordance with an embodiment. A dispenser 1000 includes a first leg 1010 and a second leg 1020, extruding from a body 1030, which may be hollow in some embodiments. The body 1030 is connected to a substantially orthogonal neck portion 1040 which is at least partially hollow, to allow storing a fluid therein. The first leg 1010 and second leg 1020 are operative for clamping onto a sidewall of an US bath system container, such as container 710 of FIG. 7. In an embodiment, the neck may taper to an opening (or extruder) 1050. When pressure inside the hollow portion of the neck 1040 is applied, fluid may be dispensed from the extruder 1050, which may be further sealed with a valve, allowing fluid 1055 to flow only under pressure, and only in a single direction (outside of the neck portion). The body 1030 includes therein an actuator 1031, which is coupled via a first shaft 1032 to a first gear 1033. The first gear 1033 is paired with a second shaft 1034, which is coupled with a piston 1035. When the actuator 1031 turns, the gear and shaft assembly cause the piston to increase pressure in the hollow neck portion 1041, in which fluid is stored. This causes fluid to exit the extruder 1050 in order to relieve the pressure created by the piston movement. The actuator 1031 may be communicatively coupled with a controller (such as controller 800 of FIG. 8) to operate the piston 1035.

Figure 11A:
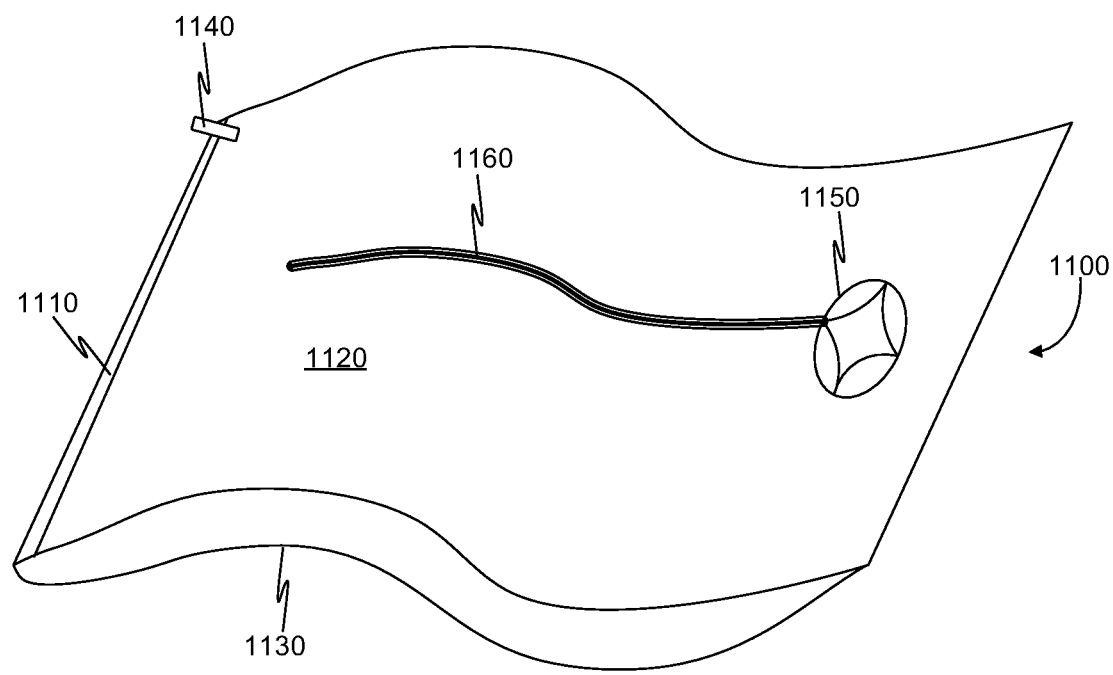
FIG. 11A—is a schematic illustration of a top front isometric view of an ultrasonic vacuum sealed enclosure, implemented in accordance with an embodiment.
Figure 11B:
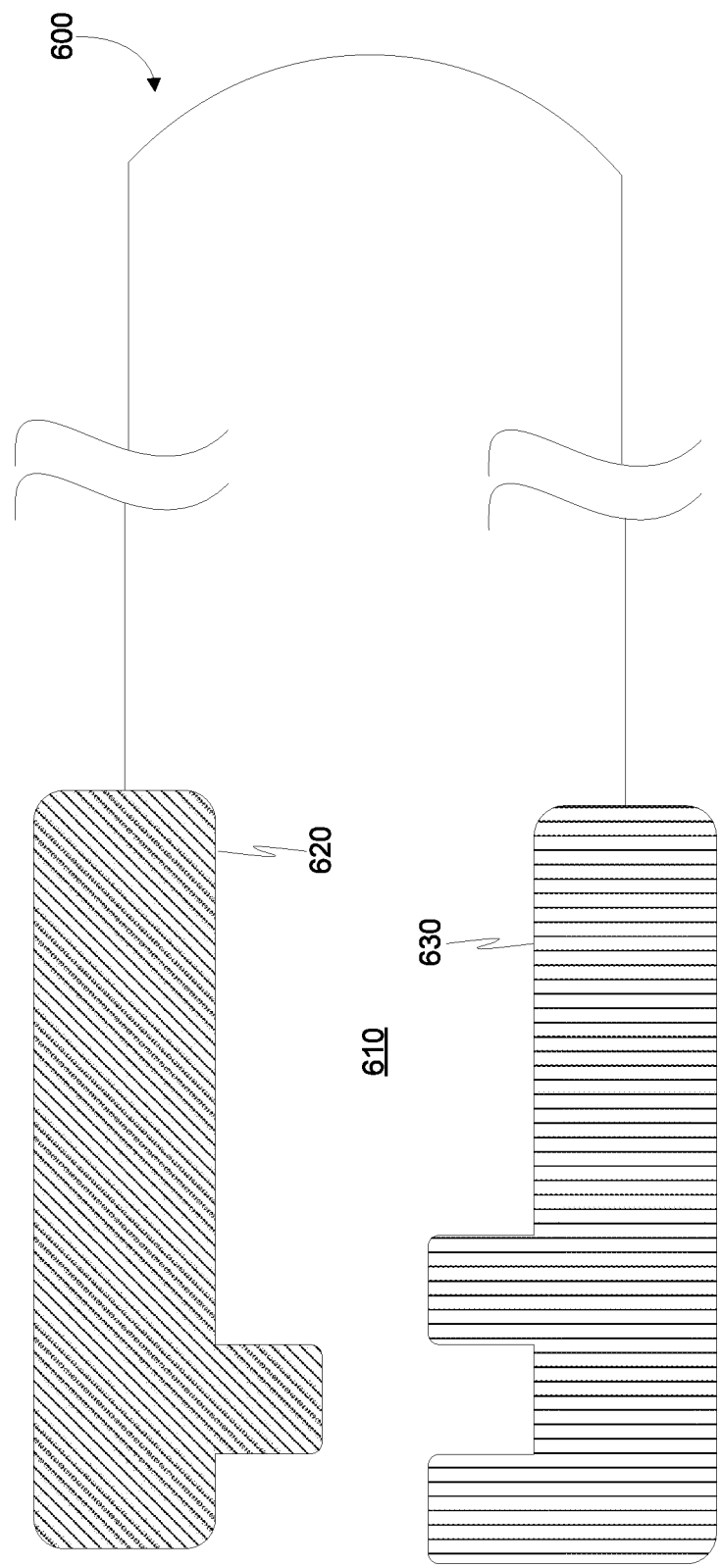
FIG. 11B—is a schematic illustration of a side view of an ultrasonic vacuum sealed enclosure, implemented in accordance with an embodiment

FIG. 11A is a schematic illustration of a top front isometric view of an ultrasonic vacuum sealed enclosure, implemented in accordance with an embodiment, and FIG. 11B is a schematic illustration of a side view of the same. An enclosure, such as a vacuum sealable bag 1100, includes an opening 1110, which is sealable by fastening the top portion 1120 of the sealed enclosure with a bottom portion 1130 of the sealed enclosure. This may be performed by fastener 1140, which can exert pressure on an edge of the top portion 1120 and bottom portion 1130, for example to lock a teeth mechanism. The vacuum sealable bag 1100 includes a unidirectional valve 1150, which allows fluids (liquids and gasses) to exit the enclosure (i.e. interior) of the bag but not enter through the same. Thus, a device which is to be disinfected/sterilized is placed in the vacuum sealable bag 1100. The bag is completely filled with a liquid solution which includes therein suspended nanoparticles of at least a first type. This can be accomplished, for example by submerging the bag while the opening 1110 is open (i.e. not fastened), then fastening the opening 1110 with the fastener 1140. In some embodiments, the vacuum sealable bag includes a metallic conductor 1160 for transmitting US waves from an US transmitter, which may be coupled to the vacuum sealable bag via the valve. For example, a tube system (not shown) may include an US transmitter and a vacuum tube, so that when the vacuum tube is connected to the valve 1150 contact is made between the US transmitter and the conductor 1160, which agitates the nanoparticles suspended in the liquid. This causes the disinfecting/sterilizing process to commence. Through the vacuum tube the liquid, and with it the contaminants, may be sucked out by applying a lower pressure. Once the tube is disconnected, the unidirectional valve 1150 does not let air or other particles in, ensuring the device stored therein remains in the disinfected/sterilized state for as long as the seal holds. In some embodiments, the enclosure may be made of an ultrasonic conducing material, to be used in place of (or additionally to) the conductor 1160. The conductor 1160 may be a substantially straight wire, a curved wire, spiral-shaped wire, combinations thereof, and the like. In some embodiments, the unidirectional valve 1150 allows for inserting a conductor 1160. In certain embodiments, the enclosure includes an opening for inserting liquid, and opening for removing the liquid, and an opening for inserting and removing a conductor attached to an US transmitter. As with FIG. 7, the embodiment discussed with respect to FIGS. 11A and 11B may likewise be used for multiple cycles.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

What is claimed is:

1. An enclosure for cleaning, disinfecting, or sterilizing an object, the enclosure comprising:
    a vacuum sealable enclosure, the enclosure comprising: a first sealable opening for inserting the object, a second opening for removing liquid from inside the enclosure, and a coupling for an ultrasonic transmitter;
    wherein the enclosure is sealed after the object is inserted, and a liquid with a first type of nanoparticles is further inserted to substantially fill the enclosure volume, wherein said nanoparticles are between 1 and 200 nanometers in size and are any combination of one or more of: metal oxides, metal nitrides and metal carbides, and wherein after the enclosure is filled with said liquid with said first type of nanoparticles, the ultrasonic transmitter is activated, and the liquid is removed, and wherein the enclosure is filled with another liquid.

2. The enclosure of claim 1, further comprising an ultrasonic conductor.

3. The enclosure of claim 1, further comprising a third opening, and wherein the liquid with said first type of nanoparticles or said other liquid is inserted into the enclosure through the third opening.

4. The enclosure of claim 1, wherein the object comprises a dental appliance placed in a tooth container or a mouthguard and said first type of nanoparticles enter said tooth container or said mouthguard and are vibrated by said ultrasonic transmitter.

5. The enclosure of claim 3, wherein the ultrasonic transmitter is inserted through any of the openings.

6. The enclosure of claim 5, wherein the ultrasonic conductor transmitter is removed after transmitting at least one cycle of ultrasonic waves from the ultrasonic transmitter.

7. The enclosure of claim 1, wherein the enclosure is comprised of an ultrasonic wave conducting material, which conducts ultrasonic waves from the ultrasonic transmitter.

8. The enclosure of claim 4, wherein said tooth container or said mouthguard is made of an elastomeric material that ensures all dental surfaces of said dental appliance intended for cleaning are all immersed in said liquid with said first type of nanoparticles.

9. The enclosure of claim 1, wherein said metal oxides are any combination of one or more of: Silicon Dioxide, Aluminum Dioxide, Magnesium Oxide, Samarium Oxide, Titanium Dioxide, and Zinc Oxide.

10. The enclosure of claim 1, wherein said metal nitrides are any combination of one or more of: Silicon Nitride and Titanium Nitride.

11. The enclosure of claim 1, wherein said metal carbides are any combination of one or more of: Silicon Carbide, Titanium Carbide, and Tungsten Carbide.

12. The enclosure of claim 1, wherein the liquid further comprises an antibacterial agent.

13. The enclosure of claim 12, wherein the antibacterial agent is any combination of one or more of: silver sulfadiazine, chlorine, copper particles, and an antibiotic.

14. The enclosure of claim 1, wherein the first type of nanoparticle comprises nanoparticles of one or more materials.

15. The enclosure of claim 1, wherein the other liquid has therein a second type of nanoparticle.

16. The enclosure of claim 1, wherein the other liquid is removed.

17. The enclosure of claim 16, wherein removal occurs after the ultrasonic transmitter is again activated.

18. The enclosure of claim 1, wherein the liquid with said first type of nanoparticles or said other liquid is any of: water and ethanol.

* * * * *